US011253231B2

(12) United States Patent
Schmitt et al.

(10) Patent No.: US 11,253,231 B2
(45) Date of Patent: Feb. 22, 2022

(54) PREGNANCY MONITORING SYSTEM AND METHOD (71) Applicant: KONINKLIJKE PHILIPS N.V., Eindhoven (NL)

(72) Inventors: Lars Schmitt, Aachen (DE); Jakob Van De Laar, Oosterhout (NL); Markus Wohlschlager, Sindelfingen (DE); Winfried Peter Kaiser, Wildberg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 108 days.

(21) Appl. No.: 16/082,699

(22) PCT Filed: Mar. 31, 2017

(86) PCT No.: PCT/EP2017/057698
§ 371 (c)(1),
(2) Date: Sep. 6, 2018

(87) PCT Pub. No.: WO2017/167968
PCT Pub. Date: Oct. 5, 2017

(65) Prior Publication Data
US 2019/0117199 A1 Apr. 25, 2019

(30) Foreign Application Priority Data

Mar. 31, 2016 (EP) .................. 16163121

(51) Int. Cl.
*A61B 8/08* (2006.01)
*A61B 8/02* (2006.01)
(Continued)

(52) U.S. Cl.
CPC .......... *A61B 8/5276* (2013.01); *A61B 5/0011* (2013.01); *A61B 5/02411* (2013.01);
(Continued)

(58) Field of Classification Search
CPC ............ A61B 2503/02; A61B 5/02411; A61B 5/0444; A61B 5/1107; A61B 5/4362;
(Continued)

(56) References Cited

U.S. PATENT DOCUMENTS

2009/0270767 A1* 10/2009 Nishihara ............. A61B 5/1118
600/595
2011/0237906 A1 9/2011 Kabakov
(Continued)

FOREIGN PATENT DOCUMENTS

| WO | 2014162135 | 10/2014 |
|---|---|---|
| WO | 2015/062851 | 5/2015 |
| WO | 2015/117049 | 8/2015 |

OTHER PUBLICATIONS

Anonymous: "File:CTG Output jpg—Wikimedia Commons", Jun. 5, 2012 (Jun. 5, 2012), XP055378496, Retrieved from the Internet: URL:https://commons.wikimedia.org/wiki/File:CTG_Output.jpg.
(Continued)

*Primary Examiner* — Eric D. Bertram
*Assistant Examiner* — Pamela M. Bays (57) ABSTRACT

The present invention relates to a pregnancy monitoring system, the system comprising a fetal monitoring transducer (20) arranged to detect fetal medical condition information; and a control device (48) comprising a motion assessment unit (50) and a signal output unit (52); wherein the fetal monitoring transducer (20) is arranged to detect fetal movement indicative information, wherein the motion assessment unit (50) is arranged to process fetal movement grading information, in addition to the fetal movement indicative information, wherein the signal output unit (52) is arranged to simultaneously output a fetal condition signal, particularly a fetal heart rate signal, and an augmented fetal movement signal based on the fetal movement indicative information and the fetal movement grading information,
(Continued)

wherein a characteristic property of the original fetal movement information is still present in the augmented fetal movement signal. The disclosure further relates to a corresponding pregnancy monitoring method.

12 Claims, 6 Drawing Sheets

(51) Int. Cl.
    *A61B 5/11*     (2006.01)
    *A61B 8/00*     (2006.01)
    *A61B 5/00*     (2006.01)
    *A61B 5/024*     (2006.01)
    *A61B 5/344*     (2021.01)

(52) U.S. Cl.
    CPC ............ *A61B 5/1107* (2013.01); *A61B 5/721* (2013.01); *A61B 5/7203* (2013.01); *A61B 5/7207* (2013.01); *A61B 5/7221* (2013.01); *A61B 8/0866* (2013.01); *A61B 8/4477* (2013.01); *A61B 5/344* (2021.01); *A61B 5/4362* (2013.01); *A61B 8/02* (2013.01); *A61B 8/4227* (2013.01); *A61B 8/4416* (2013.01); *A61B 8/463* (2013.01); *A61B 8/488* (2013.01); *A61B 8/54* (2013.01); *A61B 2503/02* (2013.01); *A61B 2562/0219* (2013.01)

(58) Field of Classification Search
    CPC ... A61B 8/0866; A61B 8/4477; A61B 8/5276; A61B 5/0011; A61B 5/7221; A61B 5/7207; A61B 5/721; A61B 5/7203
    See application file for complete search history.

(56) References Cited

U.S. PATENT DOCUMENTS

| | | |
|---|---|---|
| 2012/0150010 A1 | 6/2012 | Hayes-Gill |
| 2012/0232398 A1* | 9/2012 | Roham .............. A61B 5/02411 600/453 |
| 2016/0058363 A1* | 3/2016 | Hayes-Gill .......... A61B 5/6804 600/588 |

OTHER PUBLICATIONS

Anonymous: "Cardiotocography—Wikipedia", Jun. 1, 2017 (Jun. 1, 2017), pp. 1-5, XP055378501, Retrieved from the Internet: URL:https://en.wikipedia.org/w/index.php?title=Cardiotocography&pri ntable=yes.

* cited by examiner

PREGNANCY MONITORING SYSTEM AND METHOD

CROSS REFERENCE TO RELATED APPLICATIONS

This application is the U.S. National Phase application under 35 U.S.C. § 371 of International Application No. PCT/EP2017/057698, filed Mar. 31, 2017 published as WO 2017/167968 on Oct. 5, 2017, which claims the benefit of European Patent Application Number 16163121.3 filed Mar. 31, 2016. These applications are hereby incorporated by reference herein.

FIELD OF THE INVENTION

The present disclosure relates to a pregnancy monitoring system and to a pregnancy monitoring method for detecting medical condition information from a pregnant subject of interest. More particularly, but not intended to limit the scope of the invention, the present disclosure relates to improvements in cardiotocography devices and methods used for monitoring a fetus in a pregnant woman.

The present invention further relates to a corresponding computer program.

BACKGROUND OF THE INVENTION

US 2016/0058363 A1 discloses a method of monitoring fetal movement, comprising obtaining a signal comprising a first record of fetal movements from a first sensor device applied to a mother's abdomen, obtaining a second record of perceived fetal movements manually input by a user for a time period concurrent with the first record of fetal movement, comparing the first and second records, and providing a log of fetal movements over time based upon said comparison.

Pregnancy monitoring which may be also referred to as fetal monitoring and/or labor monitoring is commonly used in late stages of pregnancy. By way of example, during labor, physiological parameters such as fetal heart rate may be monitored so as to identify signs of fetal distress and/or fetal well-being. Prior to labor, the mother-to-be may undergo one or more medical ultrasound examinations, thereby providing fetal heart rate information, fetal movement information, fetal size information and similar information that is used to identify markers of fetal growth during pregnancy. During labor and birth, also uterine activity, particularly uterine contractions, may be monitored.

In gynecology and obstetrics, generally two medical parameters are important to assess the condition of the fetus. These two parameters are the fetal beat-to-beat heart rate, e.g. measured via an ultrasound Doppler signal, and uterus (or labor) activity. Simultaneous assessment of the fetal heart rate (FHR) and uterine activity allows an exact determination of the fetal condition. Monitoring systems that are capable of detecting both parameters are frequently referred to as cardiotocographs (CTG monitors). However, also fetal movement is considered as an indicative parameter for assessing the condition of the fetus.

By way of example, a conventional CTG device (cardiotocography device) may contain an ultrasound Doppler transducer (US transducer) for measuring fetal heart rate (FHR) and detecting fetal movements, as well as a pressure transducer (also called toco transducer, or tocodynamometer) for measuring uterine activity. Each of the transducers may be placed on the abdomen of the mother, e.g. by an elastic belt fitted around the waist or by an adhesive tape or patch. Each of the transducers may be mounted inside a respective probe. Particularly the ultrasound transducer may be manually placed and positioned so as to seek for a considerably strong signal, e.g. a considerably strong heart beat or heart rate signal. An ideal position of the ultrasound transducer at the expectant mother's abdomen may depend on an actual orientation of the fetus.

It has been observed that motion of the fetal movement transducers, e.g., due to (re)positioning of the transducer and/or due to maternal movement may cause the ultrasound transducer to falsely indicate fetal movement. As a result, fetal movement detections are usually only reliable when there are no motion artifacts.

WO 2015/062851 A1 discloses a pregnancy monitoring system and method, the system comprising a fetal monitoring transducer that detects fetal medical condition information; a first motion sensor unit associated with the fetal monitoring transducer, the first motion sensor unit comprising at least one first motion sensor; a second motion sensor unit comprising at least one second motion sensor; and a control device comprising an evaluation unit that determines relative motion between the first motion sensor unit and the second motion sensor unit, wherein the determination of relative motion is based on motion signals supplied by the at least one first motion sensor and the at least one second motion sensor. At least one of the at least one first motion sensor and the at least one second motion sensor is attachable to an abdominal region of a subject of interest.

The control device selectively permits, in an enablement mode, processing of the detected fetal medical condition information when a level of relative motion between the first motion sensor unit and the second motion sensor unit indicates stable measurement conditions. Further, the control device selectively prevents, in a suppression mode, processing of the detected fetal medical condition information when the level of relative motion between the first motion sensor unit and the second motion sensor unit indicates unstable measurement conditions.

A means of displaying CTG information involves so-called CTG traces including simultaneous mid-term or long-term charts of, for instance, a fetal heart rate signal, a uterine activity signal, an a fetal movement signal. The CTG traces may be printed on paper (involving thermal printing on thermal paper, for instance), or may be digitally stored and displayed on a (computer) monitor in an instant or delayed fashion. A typical plot or printout of the CTG signal signals involves two or three traces using the same time base. The traces are typically spaced from one another, e.g. on top of one another, in the CTG plot.

Common CTG monitoring systems, for instance, detect fetal movements as a side product from the Doppler signal based on which the fetal heart rate signal is obtained. Fetal movements may be rather complex, particularly in terms of their impact on the Doppler signal. Fetal movements may involve head movements, limb movements, but also turning and tossing of the fetal body. Further, minor specific movements, such as fetal sucking, may manifest themselves in the Doppler signal.

Therefore, common CTG monitoring systems process a potential fetal motion signal that is present in the Doppler signal and provide a basically binary output signal which may involve, for instance, so-called fetal movement blocks affirming that, in accordance with the applied algorithm, fetal movements are found to be present at the particular time instance. Hence, a binary fetal movement indication is provided.

As discussed in WO 2015/062851 A1, further non-indicative movements may cause a distortion of the fetal motion signal or even cause incorrect fetal movements indications. Non-indicative movements may involve maternal movements, displacements of the involved sensors or transducers, and movements due to the fetus' inertia level, i.e. when the fetus is moved in a delayed fashion in response to maternal movements, particularly maternal posture changes.

As a result, also the binary fetal movement indication may be afflicted with false indications.

Nevertheless, it has been observed that clinical staff including doctors, obstetricians, nurses and midwifes became familiar with the fetal movement blocks as a fundamental component of the CTG plots. Even though it is known in theory that sometimes the fetal movement indications are caused by non-fetal movement occurrences, the clinical staff appreciates the supplemental information in the CTG plot provided by the fetal movement blocks.

SUMMARY OF THE INVENTION

It is an object of the present disclosure to provide for a pregnancy monitoring system and a related method that may allow for an improved monitoring accuracy and reliability. It would be further advantageous to provide for a system and a method that are less susceptible to motion-related mismeasurements. Preferably, the system and method are suitably arranged for enabling reliable measurements also under external motion-afflicted monitoring conditions. It would be further advantageous to provide for a system and a method that are widely accepted by the operating medical staff and that do not pose major adaptive challenges. Preferably, the system can be operated with little on even no adaption or readjustment of the clinical practice, assuming that the medical staff is used to a certain type of common pregnancy monitoring systems.

In accordance with a first aspect of the present disclosure, a cardiotocographic pregnancy monitoring system is presented, the system comprising:

a fetal monitoring transducer arranged to detect fetal medical condition information and comprising at least one ultrasound sensor;

a control device comprising a motion assessment unit and a signal output unit;

a maternal monitoring transducer comprising at least one tocodynamometer transducer; and a motion evaluation unit comprising at least one motion verification transducer;

wherein the fetal monitoring transducer is arranged to detect fetal movement indicative information, wherein the motion assessment unit is arranged to process fetal movement grading information, in addition to the fetal movement indicative information, wherein the maternal monitoring transducer is arranged to detect maternal medical condition information, wherein the motion assessment unit processes the fetal movement grading information based on a motion verification signal provided by the motion evaluation unit, and wherein the signal output unit is arranged to simultaneously output a fetal condition signal, particularly a fetal heart rate signal, a maternal condition signal, particularly a uterine activity signal, and an augmented fetal movement signal based on the fetal movement indicative information and the fetal movement grading information, wherein a characteristic property of the original fetal movement information is still present in the augmented fetal movement signal.

This aspect is based on the insight that the medical staff's acceptance is crucial for implementing refined monitoring systems and/or method. It has been observed that the potentially afflicted fetal movement blocks in the CTG charts are widely accepted, even though the fetal movement information is sometimes corrupted.

In the above WO 2015/062851 A1, it is suggested to prevent the fetal movement signal is case of detected distortions that are not attributable to genuine fetal movements of interest. Hence, when the fetal movement indication in the CTG plot is prevented, e.g. due to massive maternal motion and/or further distorting artifacts, the medical staff that is used to the presence of the fetal movement blocks (whether correct indications or wrong ones) would readily conclude that no fetal motion is present which might be indicative of an emergency situation.

As an example, when an expectant mother undergoes a CTG monitoring session at the beginning of the labor stage, no immediate, permanent on-site presence of a nurse or midwife is necessary. Rather, typically some remote supervision of the CTG monitoring session will performed, e.g. from a remote nurse's room. When the expectant mother decides to walk around and/or the change her posture, it may not be unlikely that a fetal movement indication would be induced, due to the external motion involved. Fetal movements' presence is what a remote supervising nurse quite likely would conclude.

If the respective signal was suppressed, as described in WO 2015/062851 A1, the supervising nurse might feel uncomfortable and draw false conclusions, assuming that for a considerably long term no fetal movement indication is present. This might adversely affect the dissemination and acceptance of improved pregnancy monitoring systems.

Therefore, it is proposed to maintain the well-accepted layout of the CTG plot and to augment or enrich the fetal movement indications. However, this involves, as a general constraint, that excess information should be prevented which might cause uncertainty. It is therefore proposed to indicate an actual fetal movement validity indicating signal in or next to the rather simple fetal movement indications.

Hence, the medical staff still can promptly grasp a current fetal movement state which, however, now also involves reliability information. Assuming that it is indicated that the fetal movement signal is corrupted/distorted by maternal movements, for instance, though apparently a clear fetal movement indication is present, corrective action may take place. For instance, the expectant mother may be prompted to assume a more appropriate posture and/or to stop walking around.

Generally, the fetal movement grading information may be representative of unstable measurement conditions. The fetal condition signal and the augmented fetal movement signal may be displayed and/or printed in synchronism in the same CTG plot having the same time scale.

The motion assessment unit that processes the fetal movement grading information, in addition to the fetal movement indicative information, may operate in accordance with the teaching of WO 2015/062851 A1. That is, in addition to the US transducer further motions sensor units implementing motions sensors may be provided. Further, relative motion between a first motion sensor unit and a second motion sensor unit may be detected, wherein a determination of relative motion is based on motion signals supplied by at least one first motion sensor and at least one second motion sensor.

One of the sensors may be associated with or attached to the fetal monitoring transducer, e.g. the US transducer. The other sensor may be associated with or attached to the maternal monitoring transducer. More generally, the other sensor may be attached to an abdominal portion of the expectant mother, spaced away from the fetal monitoring transducer. Relative motion between the first sensor and the second sensor may indicate non-fetal movement which, however, might be reflected in the computed fetal movement indicative information. It is therefore beneficial to provide fetal movement grading information to make the operator aware of the distortions.

However, in at least some embodiments, not separate motion sensors for external (non-fetal) motion are required. Rather, already present signals may be used to assess a reliability degree of the fetal movement indications. For instance, the data obtained by the US transducer may be processed so as to assess the fetal movement indication reliability. Hence, by applying adopted evaluation algorithms, movement indication quality state information may be obtained.

For instance, several characteristic patterns in the received ultrasound Doppler signal may be indicative of non-fetal movements, or even of non-indicative small-scale fetal movements. Hence, also the already available signals may be used to detect the fetal movement grading information. Meanwhile, obstetric ultrasound technology has been further developed and improved to a level that enables more detailed examinations and evaluations.

In an exemplary embodiment, the system further comprises a maternal monitoring transducer arranged to detect maternal medical condition information, particularly uterine activity indicative information, wherein the signal output unit is arranged to simultaneously output
the fetal condition signal,
a maternal condition signal, particularly a uterine activity signal, and
the augmented fetal movement signal.

Hence, the fetal condition signal, the uterine activity signal and the augmented fetal movement signal may be displayed and/or printed in synchronism in the same CTG plot having the same time scale.

In another exemplary embodiment of the system, the augmented fetal movement signal involves a base portion including a binary signal indicating the presence of fetal movement at least substantially based on the fetal movement indicative information detected by the fetal monitoring transducer, and an augmentation portion indicating a signal quality level of the base portion. The signal quality level may be referred to as signal reliability level.

The base portion may be solely or exclusively based on the fetal movement indicative information detected by the fetal monitoring transducer. Hence, in this exemplary embodiment, the fetal movement indicative information basically corresponds to the signal which is displayed in common CTG systems that provide fetal movement blocks.

In an exemplary refinement, the augmented fetal movement signal is a ternary signal or a tertiary signal arranged to assume three states in including a movement state, a non-movement state, and a potentially distorted signal state, and wherein the motion assessment unit determines at least the potentially distorted signal state.

Hence, the medical staff can readily grasp and understand the presented information. The informative content is greatly enriched, but still clear and manageable.

In another exemplary embodiment of the system, the signal output unit is arranged to provide a simultaneous visual reading of the fetal condition signal, the uterine activity signal, and the augmented fetal movement signal, wherein the augmented fetal movement signal involves a block representation of the presence of fetal movements and a grading signal based on the grading information.

Several options of how to present a clear visual reading within the constraints of CTG devices and typical plots may be envisaged.

In an exemplary refinement, the grading signal is an embedded grading signal and includes at least one of a color change of the block representation, a pattern variation of the block representation, a shape change of the block representation, and a magnitude change of the block representation.

In another exemplary refinement, the grading signal includes a parallel trace presented in the vicinity of the block representation and in synchronism therewith.

In another exemplary refinement, the grading signal is one of a binary signal, preferably a block signal, and a multi-level signal arranged to assume a number of states that is greater than 2. However, also a multi-level signal is to be understood as a discrete signal which may assume a limited number of discrete states. Hence, no analog or quasi-analog chart shall be provided.

In another exemplary embodiment, the system further comprises a motion evaluation unit comprising at least one motion verification transducer, wherein the motion assessment unit processes the fetal movement grading information based on a motion verification signal provided by the motion evaluation unit.

In this context, reference is made to the above discussed WO 2015/062851 A1. Instead of suppressing a potentially distorted fetal movement signal, it is proposed to provide an augmented signal in accordance with the present disclosure so as to meet the medical staff's expectations and habits.

In an exemplary refinement, the motion evaluation unit comprises a first motion verification transducer and a second motion verification transducer, wherein the motion assessment unit is arranged to determine relative motion between the first motion verification transducer and the second motion verification transducer, wherein the fetal movement grading information is dependent on an actual level of relative motion.

In another exemplary refinement, the first motion verification transducer is associated with the fetal monitoring transducer, and wherein the second motion verification transducer is arranged to be attached to an abdominal region at a distance from the first motion verification transducer and preferably associated with the maternal monitoring transducer.

In another exemplary embodiment of the system, the first motion verification transducer is associated with the fetal monitoring transducer and the second motion verification transducer is associated with the maternal monitoring transducer.

In another exemplary embodiment of the system, the first motion verification transducer and the second motion verification transducer are arranged as motion sensor units involving motion sensors, and wherein the motion evaluation unit detects relative motion between a first motion sensor unit and a second motion sensor unit based on motion signals supplied by at least one first motion sensor of the first motion sensor unit and at least one second motion sensor of the second motion sensor unit In another exemplary embodiment of the system, the fetal movement grading information is further indicative of a type of movement distortion, including at least one of maternal activity, transducer shifting, delayed inertia fetal movement, and characteristic small scale fetal activities.

In another exemplary embodiment of the system, the fetal movement grading information is further indicative of a type of indicative fetal movements, including at least one of limb movements involving arm movements and leg movements, torso movements, and head movements. Further, the type of indicative fetal movements may also include the presence of kicks, rolls, etc.

For instance, the fetal movement grading information may be displayed or printed my means of symbols adjacent to the original fetal movement blocks. The symbols represent respective movement assessment quality states or respective types of movements.

In accordance with another aspect of the present disclosure, a cardiotocographic pregnancy monitoring method is presented, the method comprising the steps of:

providing a fetal monitoring transducer and detecting fetal medical condition information involving detecting fetal movement indicative information, based on ultrasound monitoring;

providing a maternal monitoring transducer and detecting maternal medical condition information, based on tocodynamometer monitoring; and controlling the monitoring process involving motion assessment and output signal generation;

wherein the motion assessment involves processing fetal movement grading information, in addition to the fetal movement indicative information, based on a motion verification signal obtained from a motion evaluation unit, wherein the output signal generation involves simultaneously providing:

a fetal condition signal, particularly a fetal heart rate signal, obtained from the fetal monitoring transducer, a maternal condition signal, particularly a uterine activity signal, obtained from the maternal monitoring transducer, and an augmented fetal movement signal based on the fetal movement indicative information and the fetal movement grading information, wherein a characteristic property of the original fetal movement information is still present in the augmented fetal movement signal.

In an exemplary embodiment of the method, the motion verification signal is indicative of an actual level of relative motion between a first motion verification transducer and a second motion verification transducer of the motion evaluation unit.

In an exemplary embodiment, the method further comprises the step of providing a maternal monitoring transducer arranged to detect maternal medical condition information, particularly uterine activity indicative information, wherein the output signal generation involves simultaneously providing:

the fetal condition signal, a uterine activity signal, and the augmented fetal movement signal.

In another exemplary embodiment of the method, the augmented fetal movement signal involves a base portion including a binary signal indication the presence of fetal movement solely based on the fetal movement indicative information detected by the fetal monitoring transducer, and an augmentation portion indicating a signal quality level of the base portion.

In yet another aspect of the present invention, there is provided a computer program which comprises program code means for causing a computer to perform the steps of the method in accordance with the present disclosure when said computer program is carried out on that computer.

As used herein, the term "computer" may stand for a large variety of processing devices. In other words, also mobile devices having a considerable computing capacity can be referred to as computing device, even though they provide less processing power resources than standard "computers". Needless to say, such a "computer" can be a part of a medical device and/or system. Furthermore, the term "computer" may also refer to a distributed computing device which may involve or make use of computing capacity provided in a cloud environment.

The term "computer" may also relate to medical technology devices, fitness equipment devices, and monitoring devices in general, that are capable of processing data. Preferred embodiments of the disclosure are defined in the dependent claims. It should be understood that the claimed method and the claimed computer program can have similar preferred embodiments as the claimed device and as defined in the dependent device claims.

Preferred embodiments of the invention are defined in the dependent claims. It shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

In the following, several embodiments of systems and method that can make use of at least some aspects of the present disclosure will be presented and elucidated in more detail.

Figure 1:
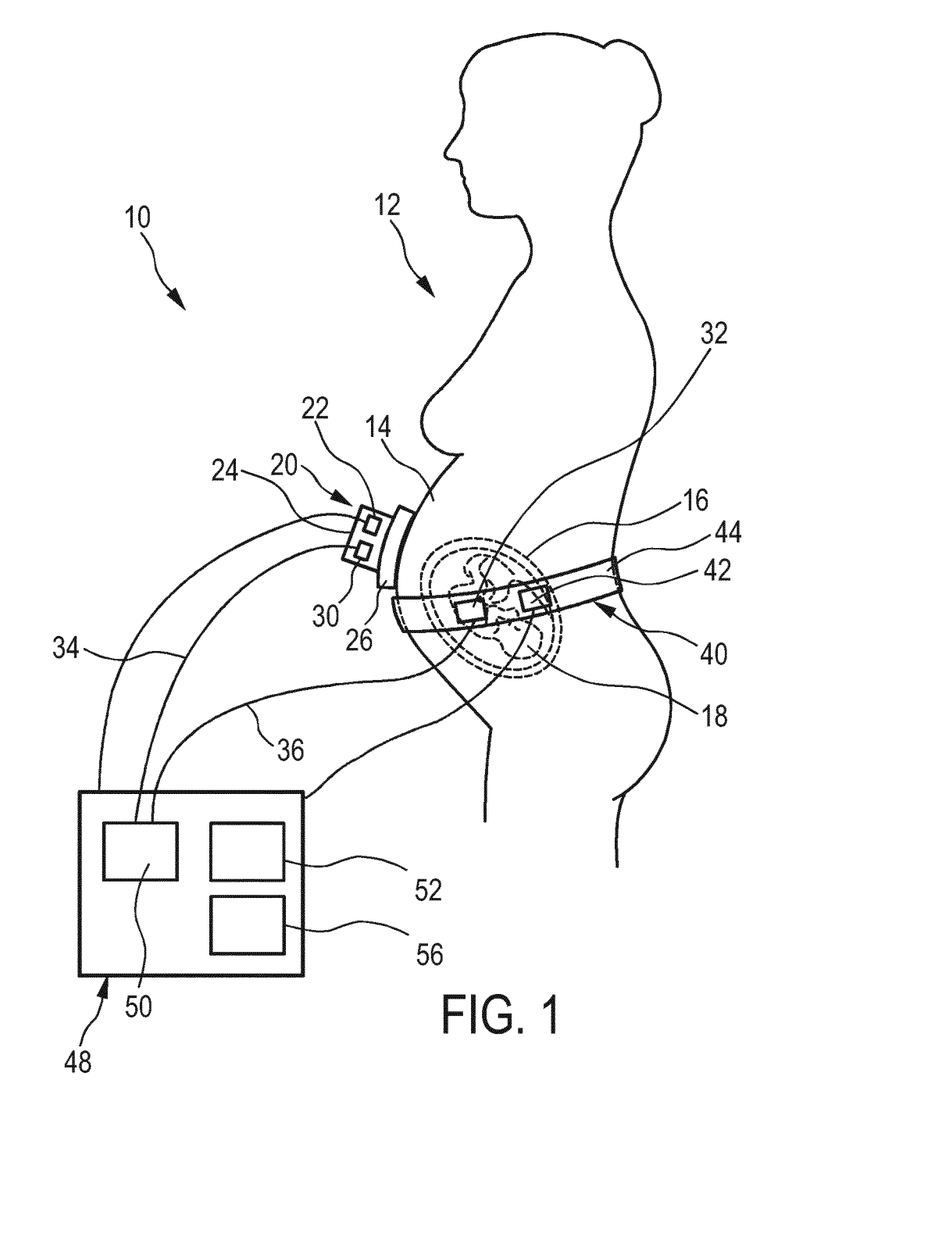
FIG. 1 shows a simplified schematic illustration of a monitoring system according to an embodiment of the present disclosure.

By way of example, FIG. 1 shows a pregnancy monitoring system 10 for monitoring a fetus 18 in a womb or uterus 16 of a to-be-monitored subject 12, particularly a pregnant female. Generally, the system 10 may be applied to an abdominal portion 14 of the subject 12. The system 10 may be capable of monitoring fetal medical condition information, such as fetal motion or, more precisely, fetal heart rate indicative signals. The system may be further capable of monitoring the subject 12, thereby obtaining maternal medical condition information, such as, for instance, uterine contractions.

The system 10 comprises a fetal monitoring transducer 20. The fetal monitoring transducer 20 may be regarded as a fetal heart rate transducer, for instance. Commonly, the fetal monitoring transducer 20 comprises at least one ultrasound sensor 22 that is capable of non-invasively detection fetal movements.

In some applications, the fetal monitoring transducer 20 may be manually guided and moved along the abdominal portion 14 of the subject 12 by an operator in order to find a strong fetal signal. It goes without saying that also any displacement of the fetal monitoring transducer 20 at the abdomen may be somehow reflected by a signal provided by the ultrasound sensor 22. Consequently, a desired fetal signal may be strongly distorted.

The fetal monitoring transducer 20 may further comprise a housing 24 to which a contact face or pad 26 may be attached. The pad 26 may be configured for contacting the abdominal skin of the subject 12 during operation. The ultrasound sensor 22 may be embedded in the housing 24. Further, at least one first motion sensor unit 30 may be associated with the fetal monitoring transducer 20. Particularly, the at least one first motion sensor unit 30 may be provided in the housing 24 as well. Consequently, the ultrasound sensor 22 and the at least one first motion sensor unit 30 may experience basically similar motion occurrences.

The system 10 may further comprise at least one second motion sensor unit 32. The at least one second motion sensor unit 32 may serve as a reference motion sensor unit 32 for the first motion sensor unit 30. The first motion sensor unit 30, the second motion sensor unit 32 and, if also provided, any further motion sensor unit may be connected to a control device 48 via respective signal connectors 34, 36 e.g. via wire-based or wireless signal lines.

The control device 48 comprises a motion assessment unit 50 and a signal output unit 52. The control device 48 as such is operable to compute fetal movement indicative information. The motion assessment unit 50 is arranged to compute fetal movement grading information, in addition to the fetal movement indicative information. The output unit 52 may be operatively coupled with a display and/or a chart printer, e.g. a thermal printer that provides a CTG plot. The information provided by the display or the printer is exemplarily shown in FIG. 4 further below.

The control device 48 may further comprise a motion evaluation unit 56 comprising at least one motion verification transducer, wherein the motion assessment unit processes the fetal movement grading information based on a motion verification signal provided by the motion evaluation unit. As used herein, the motion verification transducer may be embodied by one of the motion sensor units 30, 32.

Figure 2:
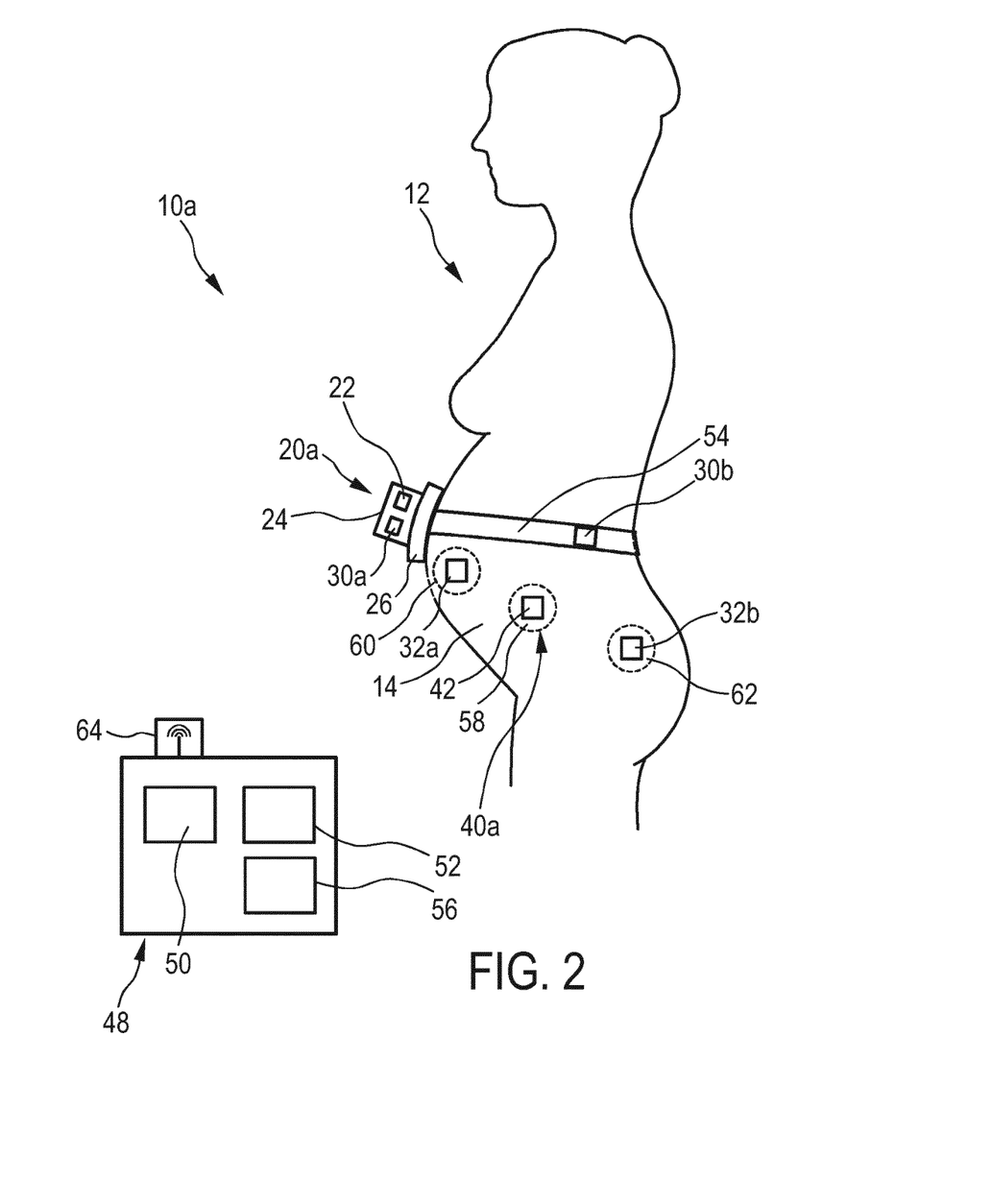
FIG. 2 shows a simplified schematic illustration of another monitoring system according to an embodiment of the present disclosure.

The motion evaluation unit 56 is exemplarily shown in FIG. 1 and FIG. 2 as forming part of the control device 48. The motion evaluation unit 56 comprises and/or is arranged to be coupled with at least one motion verification transducer. By way of example, the at least one motion verification transducer may be implemented by the at least one motion sensor unit 30, 32. In the alternative, the at least one motion verification transducer may utilize sensor data provided by the at least one motion sensor unit 30, 32.

The motion evaluation unit 56 is operatively coupled or interrelated with the motion assessment unit 50. The motion assessment unit 50 processes the fetal movement grading information based on a motion verification signal provided by the motion evaluation unit 56. However, there may be alternative embodiments, wherein the motion evaluation unit 56 is separate from but operatively coupled with the control device 48.

The motion evaluation unit 56 may be arranged to determine a level of relative motion between the motion sensor units 30 and 32. Based on this information, a motion verification signal may be provided. Based on the motion verification signal, the fetal movement grading information may be processed.

In some embodiments, the at least one second motion sensor unit 32 may be associated with a maternal monitoring transducer 40 that is capable of detecting maternal medical condition information. For instance, the maternal monitoring transducer 40 may comprise at least one tocodynamometer transducer 42 that is capable of detecting uterine contractions. Generally, the maternal monitoring transducer 40 may be connected to a respective attachment element 44, such as, for instance, a strap that may be attached to the abdominal region 14 of the subject 12. It may be preferred that the at least one second motion sensor unit 32 is associated with the maternal monitoring transducer 40. By way of example, the at least one second motion sensor unit 32 and the maternal monitoring transducer 40 may be integrated into a common housing (not shown in FIG. 1). It is generally preferred that also the maternal monitoring transducer 40, particularly the tocodynamometer transducer 42 thereof and the at least one second motion sensor unit 32 are arranged close to each other and preferably mechanically linked to each other, such that they experience basically similar motion occurrences.

FIG. 2 shows an alternative layout of a pregnancy monitoring system 10a. As can be seen in FIG. 2, a fetal monitoring transducer 20a may be provided that may basically correspond to the fetal monitoring transducer 20 illustrated in connection with FIG. 1. The fetal monitoring transducer 20a comprises a first motion sensor unit that is composed of two or more components 30a, 30b, e.g. distinct sensors, that are spaced apart from each other. By way of example, the motion sensor unit component 30a may be integrated into the housing 24 while the motion sensor unit component 30b may be attached to an attachment element or strap 54.

As can be further seen from the at least one second motion sensor unit 32a, 32b does not necessarily have to be mechanically linked to maternal monitoring transducer 40a and the tocodynamometer transducer 42, respectively. As already indicated above, also the second motion sensor unit may be composed of two or more components 32a, 32b. In some embodiments, the tocodynamometer transducer 42 and the components 32a, 32b of the second motion sensor unit may be coupled to respective attachment elements 58, 60, 62. The attachment elements 58, 60, 62 generally may be embodied by straps, adhesive strips, patches, suction caps, for instance. As can be also seen in FIG. 2, indicated by a reference number 64 designating a wireless communication module, medical condition information and motion information may be transferred wirelessly.

Figure 3:
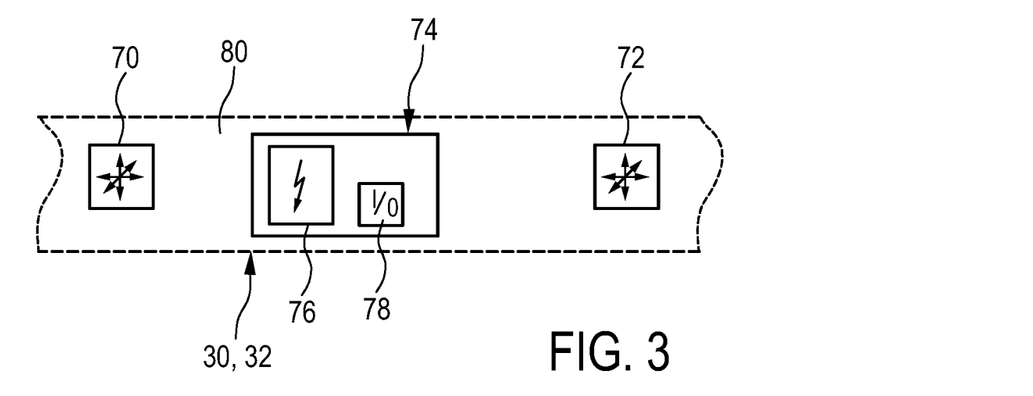
FIG. 3 shows a simplified schematic illustration of a layout of a motion sensor unit in accordance with an embodiment of the present disclosure.

FIG. 3 shows a simplified layout of a motion sensor unit 30, 32 that may generally serve as a motion sensor unit that can be associated with the fetal monitoring transducer 20 and/or the maternal monitoring transducer 40. The motion sensor unit 30, 32 may be composed of at least one motion sensor 70, 72. Each of the at least one motion sensor 70, 72 may be configured as accelerometer-based motion sensor, for instance. The motion sensor unit 30, 32 may further comprise a controller unit 74 that may be provided with a controller 76 and an input/output port 78. At least some or each of the components 70, 72, 74 may be arranged on a carrier strap 80, or in a respective housing or in another suitable way. It shall be understood that those skilled in the art may readily identify, deduce and implement similar motion sensor units 30, 32 that may be coupled to the monitoring systems 10, 10*a* so as to further improve monitoring accuracy and reliability.

It is again emphasized that in at least some embodiments, the motion assessment unit 50 does not necessarily require (external) movement information provided by separate motion sensor units 30, 32 as shown in FIG. 1 and FIG. 2. In the alternative, or in addition, the motion assessment unit 50 may be primarily provided with information detected by the fetal monitoring transducer 20 which may be arranged as an US transducer, for instance. In further exemplary embodiments, the motion assessment unit 50 is operable to process information provided by the fetal monitoring transducer 20 and information provided by the additional motion sensor units 30, 32 that detect external movements.

Figure 4:
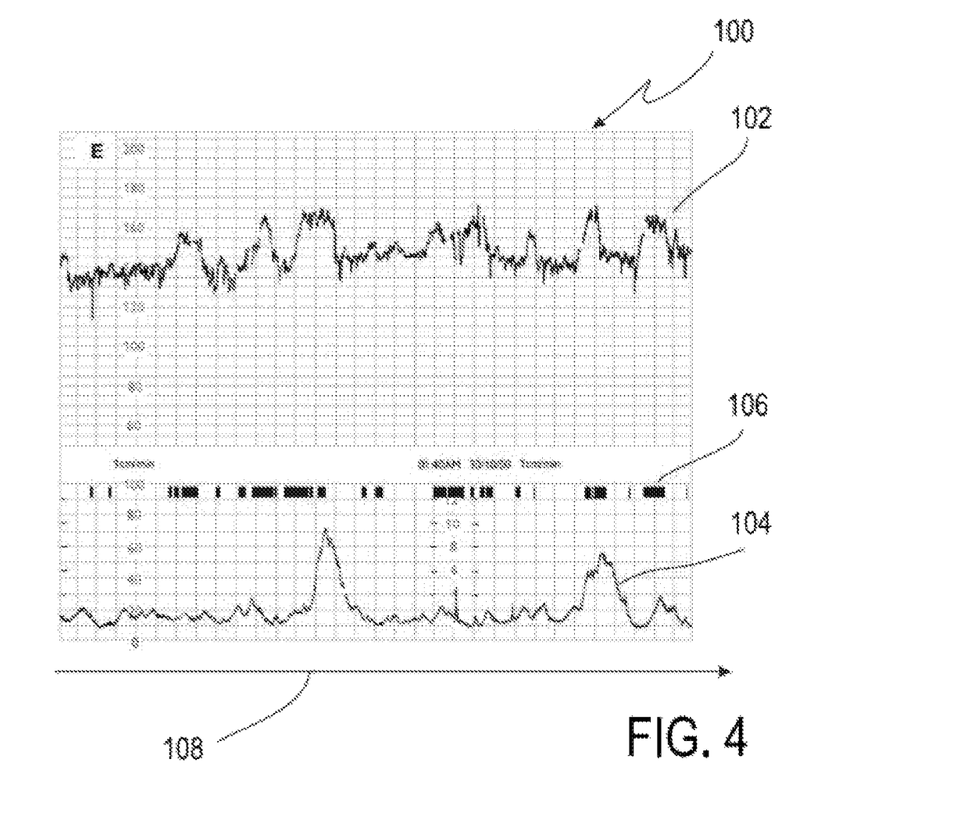
FIG. 4 shows a simplified illustration of an exemplary CTG plot involving fetal information, maternal information, and fetal movement information.

Reference is made to FIG. 4 illustrating an exemplary CTG plot 100. The plot 100 comprises signal traces 102, 104, 106 which are simultaneously recorded and presented. A common time base for the traces 102, 104, 106 is indicated by a time axis 108.

The trace 102 represents a fetal condition signal, particularly a fetal heart rate signal. The trace 104 represents a maternal condition signal, particularly a uterine activity signal. Further, the trace 106 represents fetal movements which are indicative of fetal activity and fetal well-being. The trace 106 involves a block representation. Consequently, the presented information is generally referred to as fetal movement blocks. The trace 106 represents a binary signal that is arranged to assume two states, namely a first state where no fetal movements are present, and a second state where fetal movements are present. As already discussed above, the trace 106 may involve wrong indications, e.g. due to external movements and/or signal distortion.

Figure 5:
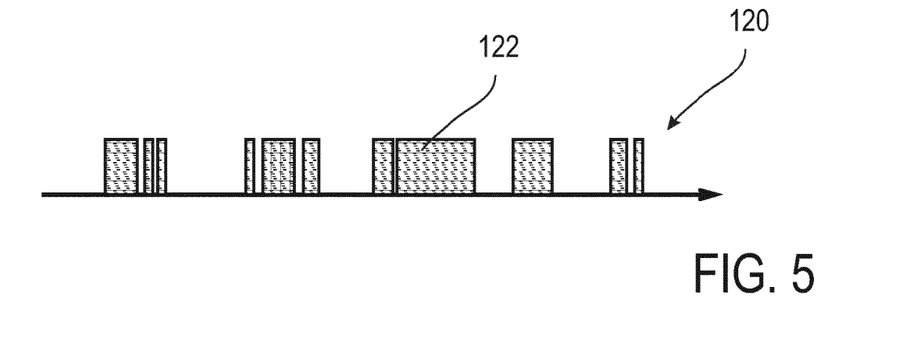
FIG. 5 shows an exemplary fetal movement trace.

FIG. 5 illustrates a schematic simplified representation of a fetal movement trace or plot 120 in accordance with the binary trace 106 of the CTG plot 100 of FIG. 4. The plot 120 is composed of blocks 122 indicating the presence of fetal movements.

In accordance with the present disclosure, it is proposed to augment or enrich the plot 120. Hence, a modified of augmented CTG plot can be provided.

Figure 6:
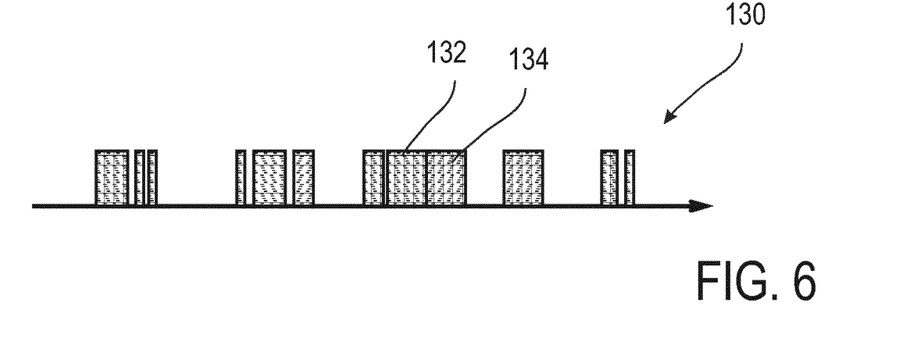
FIG. 6 shows an exemplary embodiment of an augmented fetal movement plot.

For instance, a modified augmented signal 130 is shown in FIG. 6. Still, the signal 130 is composed of blocks 132, 134. However, the blocks 132, 134, while still having the same height, are visually distinguishable and may have a different pattern, color, and such like.

For instance, the pattern of block 132 indicates the presence of fetal movements at a sufficiently high reliability level. By contrast, the block 134 may indicate potential movements which may be however attributable to non-fetal movement, e.g. maternal movements, transducer movements/dislocations, etc.

Hence, in accordance with the computed actual level of the fetal movement grading information, it can be assessed whether the reliability level is sufficiently high. If this is the case, the genuine movement signal 132 may be provided. In case where the level of reliability is not sufficiently high, but where nevertheless movement indications are present, the signal 134 involving distinct blocks may clearly indicate the reduced reliability condition.

The medical staff which is used to binary signals as shown in FIG. 5 does not face major challenges in grasping, understanding and finally accepting the augmented signal representation.

Figure 7:
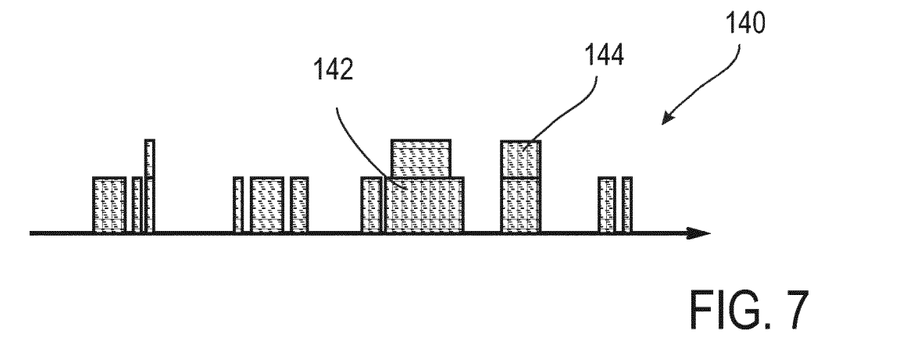
FIG. 7 shows another exemplary embodiment of an augmented fetal movement trace.

Similarly, also FIG. 7 illustrates an augmented fetal movement signal 140 where the shape, particularly the height or magnitude of involves blocks 142, 144 is different. The signal 140 is a ternary signal that can assume three states.

A first state indicates that no movements at all are present which may involve movements that do not exceed a defined negligibility threshold. A second state is indicated by the pattern of block 142 and indicates that fetal movements are present at a defined first accuracy level. A third state is indicated by the pattern of block 144 and indicates that fetal movements are present at a defined second accuracy level.

Figure 8:
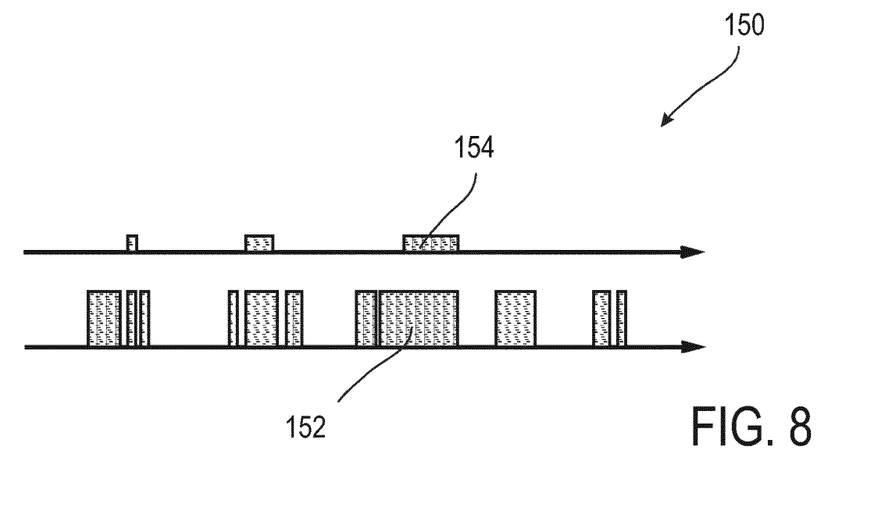
FIG. 8 shows another exemplary embodiment of an augmented fetal movement trace.

FIG. 8 illustrates a similar augmented fetal movement signal 150 which however comprises a first binary signal plot involving blocks 152 and a second (top) binary signal plot involving blocks 154. As the signal of the second plot may not be enabled when the signal of the first (bottom) plot is not enabled, a three-state or tertiary presentation is provided. The first plot basically corresponds to the plot of FIG. 5. The second plot provides supplemental fetal movement grading information.

Figure 9:
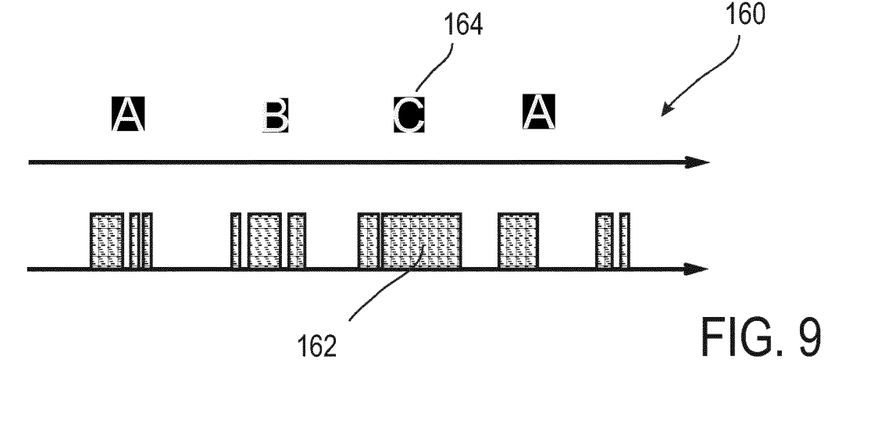
FIG. 9 shows another exemplary embodiment of an augmented fetal movement trace.

Further reference is made to FIG. 9 illustrating an augmented fetal movement signal 160 which comprises a first binary signal plot involving blocks 162. Further, symbols 164 are present which are shown in FIG. 9 in an upper plot as capital letters, for illustrative purposes. Rather, icons and graphic symbols may be used so as to improve the comprehensibility of the augmented signals.

The symbols 164 may provide multi-level or multi-stage information including a type of movement distortion, involving at least one of maternal activity, transducer shifting, delayed inertia fetal movement, and characteristic small scale fetal activities. An example for a small-scale fetal activity is fetal thumb-sucking or fist-sucking.

Hence, the symbols indicate a reduced reliability level of the first binary signal plot but also provide further information as to potential sources of the signal distortions.

In some embodiments, the symbols 164 also may be used in cases where the accuracy level is sufficiently high, as genuine (non-distorted) fetal movements have been detected. In these cases, the symbols 164 may for instance indicate the type of fetal movement, e.g. leg movement, kicks, rolling, arm movement, torso movements, head movements, etc.

As already indicated above, the type of movement may be reflected in the received US signal. Hence, characteristic patterns indicate a certain type of movement.

An augmented fetal movement signal based on the fetal movement indicative information and the fetal movement grading information is provided, wherein a characteristic property of the original fetal movement information is still present in the augmented fetal movement signal.

A further benefit of the simultaneous presentation of fetal movement indications and the fetal movement grading information is that a frequency of occurrences of unstable measurement conditions, if any, can be detected. This provides the medical staff with additional information on the activity of the mother, which for instance may support further clinical decisions or actions (e.g. prompting the mother to assume a more resting position in case better CTG quality is desired).

Figure 10:
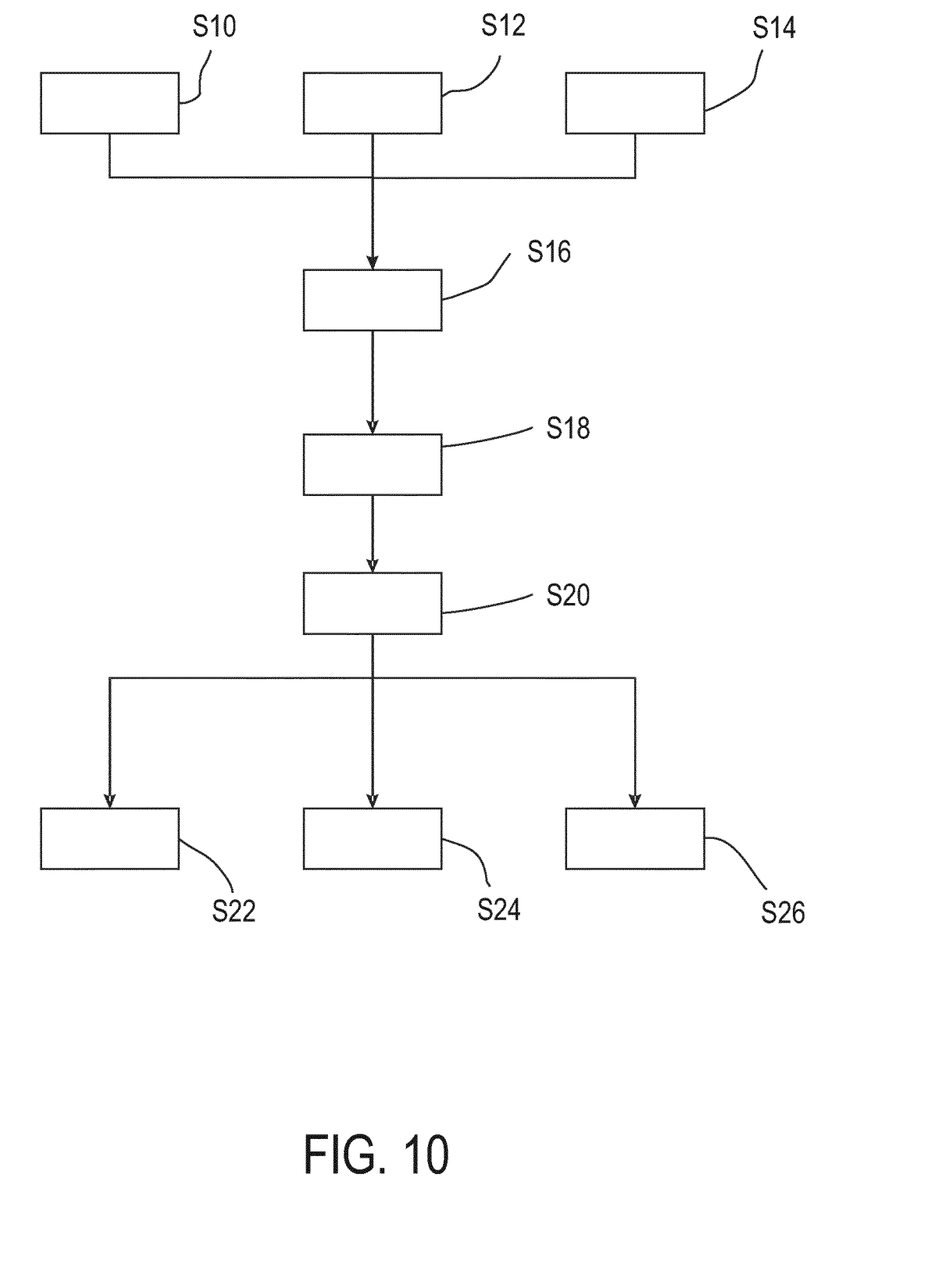
FIG. 10 shows an illustrative block diagram representing several steps of an embodiment of a method in accordance with the present disclosure.

Further reference is made to FIG. 10 schematically illustrating an exemplary embodiment of a method for enhanced pregnancy monitoring in accordance with the present disclosure.

A step S10 relates to the provision of a fetal monitoring transducer that is arranged to detect fetal medical condition information, particularly a fetal heart rate signal. Further, the fetal monitoring transducer may detect fetal movement indicative information. The fetal monitoring transducer may be arranged as an US Doppler transducer.

An optional step S12 relates to the provision of a maternal monitoring transducer that is arranged to detect maternal medical condition information, particularly uterine activity indicative information. The maternal monitoring transducer may be arranged as a tocodynamometer transducer.

A further optional step S14 relates to the provision of addition (external) motion sensor units which may be associated with the fetal monitoring transducer and/or the maternal monitoring transducer. Further, also distinct motion sensor units may be provided which can be attached to an abdominal portion of an expectant mother.

A further step S16 relates to an initiation of a pregnancy monitoring session, particularly a CTG examination. The pregnancy monitoring examination involves at least monitoring a fetal condition signal and fetal movement indicative information.

The examination involves a step S18 which includes an augmented motion assessment which may involve a reliability assessment. Motion assessment involves processing fetal movement grading information.

Further, an output step S20 is provided which typically involves a simultaneous output of a fetal condition signal, particularly a fetal heart rate signal (step S22), a maternal condition signal, particularly a uterine activity indicative signal (step S24), and an augmented fetal movement signal based on the fetal movement indicative information and the fetal movement grading information (step S26).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A cardiotocographic pregnancy monitoring system, comprising:
    a fetal monitoring transducer arranged to detect fetal medical condition information and comprising at least one ultrasound sensor;
    a control device comprising a motion assessment unit and a signal output unit;
    a maternal monitoring transducer comprising at least one tocodynamometer transducer; and
    a motion evaluation unit comprising a first motion verification transducer being associated with the fetal monitoring transducer and a second motion verification transducer being associated with the maternal monitoring transducer;
    wherein the fetal monitoring transducer is arranged to detect fetal movement indicative information,
    wherein the motion assessment unit is arranged to process, in addition to the fetal movement indicative information, fetal movement grading information by determining relative motion between the first motion verification transducer and the second motion verification transducer, wherein the fetal movement grading information is dependent on an actual level of relative motion and is indicative of a movement quality state,
    wherein the fetal movement grading information includes a plurality of reliability levels of the fetal movement indicative information, wherein a first reliability level of the plurality of reliability levels corresponds to a distorted fetal movement identified in the fetal movement indicative information and a second reliability level of the plurality of reliability levels corresponds to an undistorted fetal movement identified in the fetal movement indicative information,
    wherein the maternal monitoring transducer is arranged to detect maternal medical condition information,
    wherein the motion assessment unit processes the fetal movement grading information based on a motion verification signal provided by the motion evaluation unit, and
    wherein the signal output unit is arranged to simultaneously output:
        a fetal condition signal,
        a maternal condition signal, and
        an augmented fetal movement signal based on the fetal movement indicative information and the fetal movement grading information, wherein a characteristic property of the fetal movement indicative information is still present in the augmented fetal movement signal, wherein the augmented fetal movement signal represents the plurality of reliability levels of the fetal movement indicative information to simultaneously display the plurality of reliability levels in relation to the characteristic property of the fetal movement indicative information.

2. The system as claimed in claim 1, wherein the augmented fetal movement signal involves a base portion including a binary signal indicating a presence of fetal movement substantially based on the fetal movement indicative information detected by the fetal monitoring transducer, and an augmentation portion indicating a signal quality level of the base portion.

3. The system as claimed in claim 2, wherein the augmented fetal movement signal is a ternary signal or a tertiary signal arranged to assume three states in including a movement state, a non-movement state, and a potentially distorted signal state, and wherein the motion assessment unit determines at least the potentially distorted signal state.

4. The system as claimed in claim 1, wherein the signal output unit is arranged to provide a simultaneous visual reading of the fetal condition signal, a uterine activity signal, and the augmented fetal movement signal, and wherein the augmented fetal movement signal involves a block representation of a presence of fetal movements and a grading signal based on the fetal movement grading information.

5. The system as claimed in claim 4, wherein the grading signal is an embedded grading signal and includes at least one of a color change of the block representation, a pattern variation of the block representation, a shape change of the block representation, and a magnitude change of the block representation.

6. The system as claimed in claim 4, wherein the grading signal includes a parallel trace presented in the vicinity of the block representation and in synchronism therewith.

7. The system as claimed in claim 4, wherein the grading signal is one of a binary signal, and a multi-level signal arranged to assume a number of states that is greater than 2.

8. The system as claimed in claim 7, wherein the grading signal is a block signal.

9. The system as claimed in claim 1, wherein the first motion verification transducer and the second motion verification transducer are arranged as motion sensor units involving motion sensors, and wherein the motion evaluation unit detects relative motion between a first motion sensor unit and a second motion sensor unit based on motion signals supplied by at least one first motion sensor of the first motion sensor unit and at least one second motion sensor of the second motion sensor unit.

10. The system as claimed in claim 1, wherein the fetal movement grading information is further indicative at least one of maternal activity, transducer shifting, delayed inertia fetal movement, or characteristic small scale fetal activities.

11. The system as claimed in claim 1, wherein the fetal condition signal is a fetal heart rate signal.

12. The system as claimed in claim 1, wherein the maternal condition signal is a uterine activity signal.

* * * * *